(12) United States Patent
Takahashi et al.

(10) Patent No.: US 11,754,728 B2
(45) Date of Patent: Sep. 12, 2023

(54) X-RAY IMAGING APPARATUS AND CONTROL METHOD OF X-RAY IMAGING APPARATUS

(71) Applicant: Sharp Display Technology Corporation, Kameyama (JP)

(72) Inventors: Kohzoh Takahashi, Kameyama (JP); Akinori Kubota, Kameyama (JP)

(73) Assignee: SHARP DISPLAY TECHNOLOGY CORPORATION, Kameyama (JP)

( * ) Notice: Subject to any disclaimer, the term of this patent is extended or adjusted under 35 U.S.C. 154(b) by 0 days.

(21) Appl. No.: 17/830,479

(22) Filed: Jun. 2, 2022

(65) Prior Publication Data
US 2022/0390626 A1    Dec. 8, 2022

(30) Foreign Application Priority Data
Jun. 7, 2021 (JP) ................................ 2021-095281

(51) Int. Cl.
*G01T 1/20* (2006.01)
*G01T 1/208* (2006.01)
*A61B 6/00* (2006.01)
*H01L 27/146* (2006.01)

(52) U.S. Cl.
CPC ............ *G01T 1/2018* (2013.01); *A61B 6/485* (2013.01); *A61B 6/548* (2013.01); *G01T 1/208* (2013.01); *H01L 27/14663* (2013.01)

(58) Field of Classification Search
CPC ......... G01T 1/2018; G01T 1/208; G01T 1/20; A61B 6/485; A61B 6/548; A61B 6/40; A61B 6/54; A61B 6/586; A61B 6/4208; A61B 6/585; H01L 27/14663; G03B 42/02; H04N 5/20; H04N 5/32

See application file for complete search history.

(56) References Cited

U.S. PATENT DOCUMENTS

| 2005/0173645 | A1* | 8/2005 | Endo ................. | H01L 27/14658 250/370.11 |
| 2011/0204246 | A1 | 8/2011 | Tanaka et al. | |
| 2014/0348299 | A1* | 11/2014 | Sung .................. | H04N 23/6812 378/91 |
| 2016/0284748 | A1* | 9/2016 | Mruthyunjaya .. | H01L 27/14614 |

FOREIGN PATENT DOCUMENTS

| JP | 2004-521721 A | 7/2004 |
| JP | 2011-176235 A | 9/2011 |
| JP | 2012-134781 A | 7/2012 |
| WO | 03/021294 A1 | 3/2003 |

* cited by examiner

*Primary Examiner* — Kiho Kim
(74) *Attorney, Agent, or Firm* — KEATING & BENNETT, LLP

(57) ABSTRACT

An X-ray imaging apparatus includes an X-ray source, an X-ray imaging panel, and a controller. The controller includes an image processing unit that generates an inspection image in accordance with a data signal read from a thin-film transistor with the thin-film transistor supplied with a gate signal, a detection control unit that detects a dark-spot pixel from the inspection image, and a threshold correction unit that applies, to a gate of the thin-film transistor corresponding to the dark-spot pixel, a positive shift voltage that raises a gate-off threshold voltage of the thin-film transistor.

5 Claims, 13 Drawing Sheets

| No. | GATE LINE NUMBER | DATA LINE NUMBER |
|---|---|---|
| 1 | 542 | 475 |
| 2 | 841 | 643 |
| ... | ... | ... |

| No. | GATE LINE NUMBER | DATA LINE NUMBER | DEGREE OF NEGATIVE SHIFTING |
|---|---|---|---|
| 1 | 542 | 475 | B1 |
| 2 | 841 | 643 | B2 |
| ... | ... | ... | ... |

X-RAY IMAGING APPARATUS AND CONTROL METHOD OF X-RAY IMAGING APPARATUS

BACKGROUND

1. Field

The present disclosure relates to an X-ray imaging apparatus and a control method of the X-ray imaging apparatus.

2. Description of the Related Art

X-ray imaging apparatuses with thin-film transistors and control methods of the X-ray imaging apparatuses are disclosed. For example, Japanese Unexamined Patent Application Publication (Translation of PCT Application) No. 2004-521721 discloses an X-ray imaging apparatus and a control method of the X-ray imaging apparatus.

In the X-ray imaging apparatus (solid-state X-ray detector) disclosed in Japanese Unexamined Patent Application Publication (Translation of PCT Application) No. 2004-521721, part of the solid-state X-ray detector is covered with a radiation shielding material. An exposed portion of the solid-state X-ray detector is irradiated with radiation (X rays) at a level high enough for the radiation to reach a predetermined threshold. The solid-state X-ray detector acquires an X-ray image and determines whether there is an line artifact. Information on a data line of interest that has been determined to have a line artifact is stored on an image processor. The pixel value of a pixel connected to the data line that has been determined to have the line artifact is replaced with the mean value of pixel values of two data lines adjacent to the data line of interest. In this way, even when thin-film transistors in the solid-state X-ray detector have larger leakage currents, pixel values of multiple pixels including a pixel connected to a data line likely to have an artifact may thus be corrected.

The disclosed X-ray imaging apparatus employs an X-ray source (higher-powered X-ray source) that is enabled to emit higher powered X rays creating line artifacts than X rays emitted by an X-ray source typically used for X-ray imaging. In the disclosed X-ray imaging apparatus, pixel values of all pixels connected to the data line of interest that is determined to display artifacts are replaced with a mean value of pixel values of pixels connected to two data lines adjacent to the data line of interest. For this reason, in the disclosed X-ray imaging apparatus, the pixel values of pixels that are originally free from any correction are replaced with different values (corrected with different values).

It is desirable to provide an X-ray imaging apparatus and a control method of the X-ray imaging apparatus that are enabled to enhance image quality on each pixel without employing a higher-powered X-ray source.

SUMMARY

According to a first aspect of the disclosure, there is provided an X-ray imaging apparatus including: an X-ray source; an X-ray imaging panel including a scintillator that converts X rays emitted from the X-ray source into light, a photoelectric conversion element that converts the light from the scintillator into an electrical signal, and a thin-film transistor connected to the photoelectric conversion element; and a controller that controls emission of the X rays from the X-ray source and imaging performed by the X-ray imaging panel. The controller includes: an image processing unit that generates an inspection image that is captured with a subject not placed between the X-ray source and the X-ray imaging panel in accordance with a data signal that is read from the thin-film transistor supplied with a gate signal; a detection control unit that detects a dark-spot pixel from the inspection image; and a threshold correction unit that applies, to a gate of a thin-film transistor corresponding to the dark-spot pixel, a positive shift voltage that raises a gate-off threshold voltage of the thin-film transistor.

According to a second aspect of the disclosure, there is provided a control method of an X-ray imaging apparatus including an X-ray source, and an X-ray imaging panel that includes a scintillator that converts X rays emitted from the X-ray source into light, a photoelectric conversion element that converts the light from the scintillator into an electrical signal, and a thin-film transistor connected to the photoelectric conversion element. The control method includes: irradiating the X-ray imaging panel with the X rays from the X-ray source; acquiring an inspection image that is captured with a subject not placed between the X-ray source and the X-ray imaging panel in accordance with a data signal that is read from the thin-film transistor supplied with a gate signal; detecting a dark-spot pixel from the inspection image; and applying, to a gate of a thin-film transistor corresponding to the dark-spot pixel, a positive shift voltage that raises a gate-off threshold voltage of the thin-film transistor.

DESCRIPTION OF THE EMBODIMENTS

Figure 1:
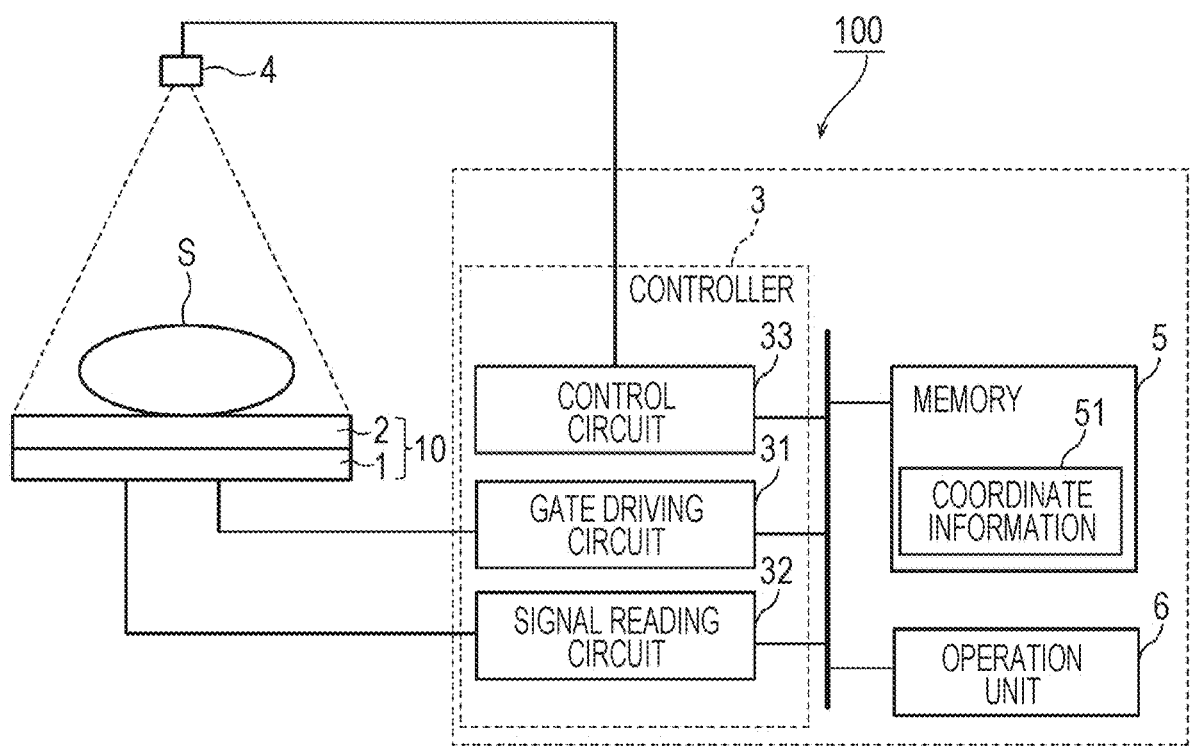
FIG. 1 illustrates an X-ray imaging apparatus of a first embodiment.

Embodiments of the disclosure are described with reference to the drawings. The disclosure is not limited to the embodiments described below. The embodiments may be appropriately modified without departing from the scope of the disclosure. In the discussion that follows, like elements or elements having the same function are designated with the same reference numerals throughout the drawings and the discussion thereof are not repeated. Configurations in the embodiments and modifications of the embodiments may be combined or changed without departing from the scope of the disclosure. For easier understanding, the configurations may be simplified or clarified in the drawings, and some of components in each configuration may be omitted. The components in the drawings are not necessarily drawn according to the actual dimensional ratio.

Configuration of First Embodiment

FIG. 1 illustrates a configuration of an X-ray imaging apparatus 100 of a first embodiment. The X-ray imaging apparatus 100 includes an X-ray imaging panel 10 including a photoelectric conversion panel 1 and a scintillator 2, a controller 3, an X-ray source 4, a memory 5, and an operation unit 6.

The controller 3 includes a gate driving circuit 31, a signal reading circuit 32, and a control circuit 33. The gate driving circuit 31 and the signal reading circuit 32 are connected to the photoelectric conversion panel 1. The control circuit 33 is connected to the gate driving circuit 31, the signal reading circuit 32, and the X-ray source 4. The control circuit 33 includes a processor that executes a program stored on the memory 5. The control circuit 33 causes the X-ray source 4 to emit X rays and control the imaging performed by the X-ray imaging panel 10.

The X-ray source 4 irradiates a subject S with X rays. The X rays transmitted through the subject S are converted into fluorescence (hereinafter referred to as scintillation light) by the scintillator 2 that is mounted on the photoelectric conversion panel 1. The X-ray imaging apparatus 100 picks up the scintillation light with the X-ray imaging panel 10, and creates a captured X-ray image with the controller 3.

The memory 5 includes, for example, a non-volatile memory. The memory 5 stores a program to be executed by the control circuit 33 and coordinate information 51 on dark-spot pixels B (see FIG. 6). The dark-spot pixel B will be described with reference to FIG. 6 and the coordinate information 51 will be described with reference to FIG. 7.

The operation unit 6 includes a touch panel receiving an operation of a user or an operation panel having multiple buttons. The operation unit 6 receives from a user an operation that selects between a "standard imaging mode" and a "threshold correction mode."

In the standard imaging mode, with the subject S placed between the X-ray source 4 and the X-ray imaging panel 10, an X-ray image is created with the X-ray source 4 emitting the X rays on the X-ray imaging panel 10. In the threshold correction mode, a series of the following operations is performed. The X-ray source 4 irradiates the X-ray imaging panel 10 with X rays with the subject S not placed between the X-ray source 4 and the X-ray imaging panel 10 to generate a X-ray image (inspection image R). The dark-spot pixel B is detected and a positive shift voltage Vh is applied to the gate of a thin-film transistor (TFT) 14 corresponding to the dark-spot pixel B. A gate-off threshold voltage Vth of the TFT 14 thus shifts in a positive direction (rises).

Figure 2:
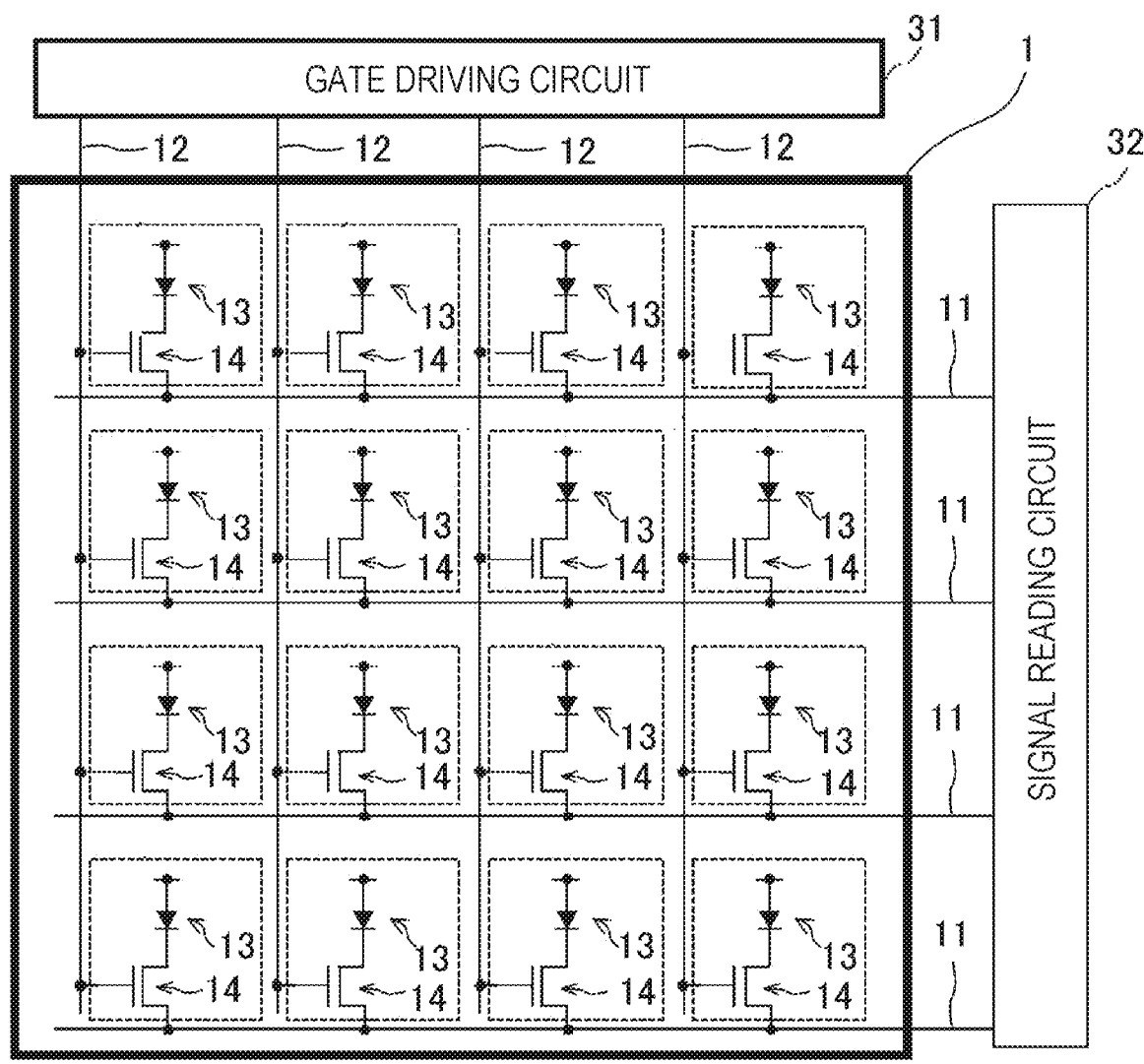
FIG. 2 illustrates a configuration of a photoelectric conversion panel.

FIG. 2 schematically illustrates a structure of the photoelectric conversion panel 1. The photoelectric conversion panel 1 includes multiple data lines 11 and multiple gate lines 12. A photodiode 13 and a thin-film transistor (TFT) 14 are arranged in each region enclosed by each data line 11 and each gate line 12. The region corresponds to a pixel that serves as a minimum unit of an image forming a captured X-ray image (a captured inspection image R). The photodiodes 13 and the TFTs 14 are arranged in a matrix. The photodiode 13 converts the scintillation light, into which the X rays transmitted through the subject S are converted, into charge responsive to an amount of the scintillation light. The gate lines 12 in the photoelectric conversion panel 1 are supplied with a gate signal from the gate driving circuit 31 such that the gate lines 12 are successively set to a selection state and the TFT 14 connected to the gate line 12 in the selection state is turned on. When the TFT 14 is turned on, a signal responsive to the charge converted by the photodiode 13 is output as a data signal to the signal reading circuit 32 via the data line 11. The TFTs 14 include a semiconductor layer manufactured of oxide semiconductor containing indium In, gallium Ga, and zinc Zn at a predetermined ratio.

Figure 3:
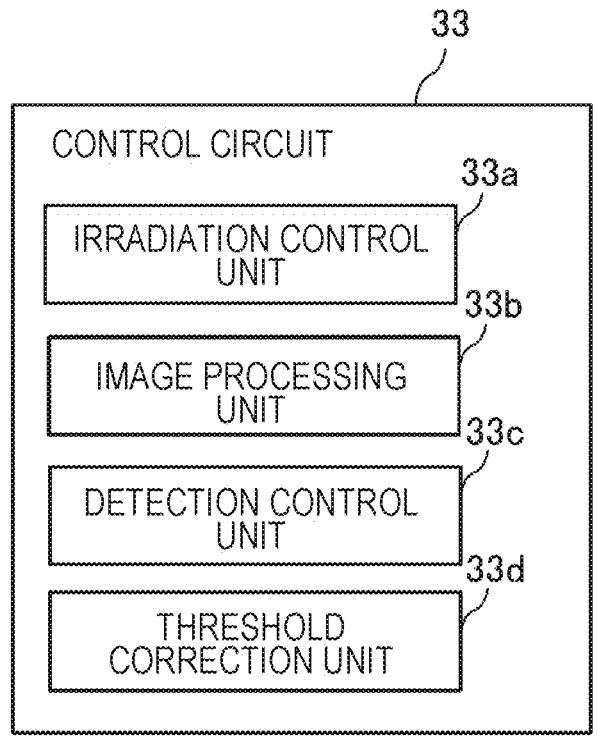
FIG. 3 is a functional block diagram illustrating a control circuit.

FIG. 3 is a functional block diagram of the control circuit 33. Referring to FIG. 3, by executing a program stored on the memory 5, the control circuit 33 functions as an irradiation control unit 33a, an image processing unit 33b, a detection control unit 33c, and a threshold correction unit 33d. In FIG. 3, the irradiation control unit 33a, the image processing unit 33b, the detection control unit 33c, and the threshold correction unit 33d are functional blocks. Alternatively, a control circuit may be arranged for each of the functions of the irradiation control unit 33a, the image processing unit 33b, the detection control unit 33c, and the threshold correction unit 33d.

The irradiation control unit 33a causes the X-ray source 4 to irradiate the X-ray imaging panel 10 with X rays in the standard imaging mode with the subject S placed between the X-ray imaging panel 10 and the X-ray source 4. According to the first embodiment, the irradiation control unit 33a causes the X-ray source 4 to irradiate the X-ray imaging panel 10 with X rays in the threshold correction mode with the subject S not placed between the X-ray imaging panel 10 and the X-ray source 4.

The image processing unit 33b controls the gate driving circuit 31 to supply a gate signal to the TFT 14 and generates the X-ray image in accordance with a data signal that the signal reading circuit 32 has read from the TFT 14. Specifically, the image processing unit 33b sets a pixel value of each pixel responsive to a voltage value of the data signal.

Figure 4:
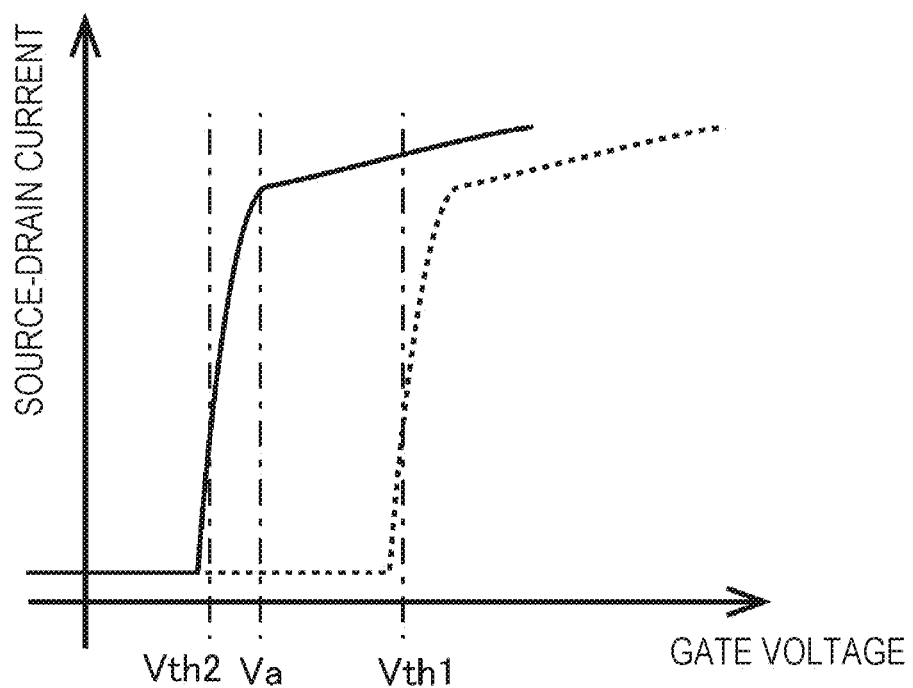
FIG. 4 illustrates a change in characteristics of a thin-film transistor (TFT)

FIG. 4 illustrates a change in characteristics of the TFT 14. A broken-line curve in FIG. 4 represents the characteristics of a new TFT 14 that is not irradiated with X rays and a solid-line curve in FIG. 4 represents the characteristics of a TFT 14 that has been used through repeated irradiation with X rays. Referring to FIG. 4, if the TFT 14 is repeatedly irradiated with X rays, the threshold of the gate-off voltage may drop, for example, from Vth1 to Vth2 (shifts in a negative direction). If the gate-off threshold voltage Vth drops below a gate-off voltage Va of the gate signal supplied from the gate driving circuit 31, the TFT 14 does not turns off (but turns on), creating a leakage current (causing charge of the photodiode 13 to be drained). As a result, a pixel at a position irradiated with X-rays in the captured X-ray image generated by the image processing unit 33b is set to a lower pixel value, becoming a pixel of dark spot (the dark-spot pixel B).

Figure 5:
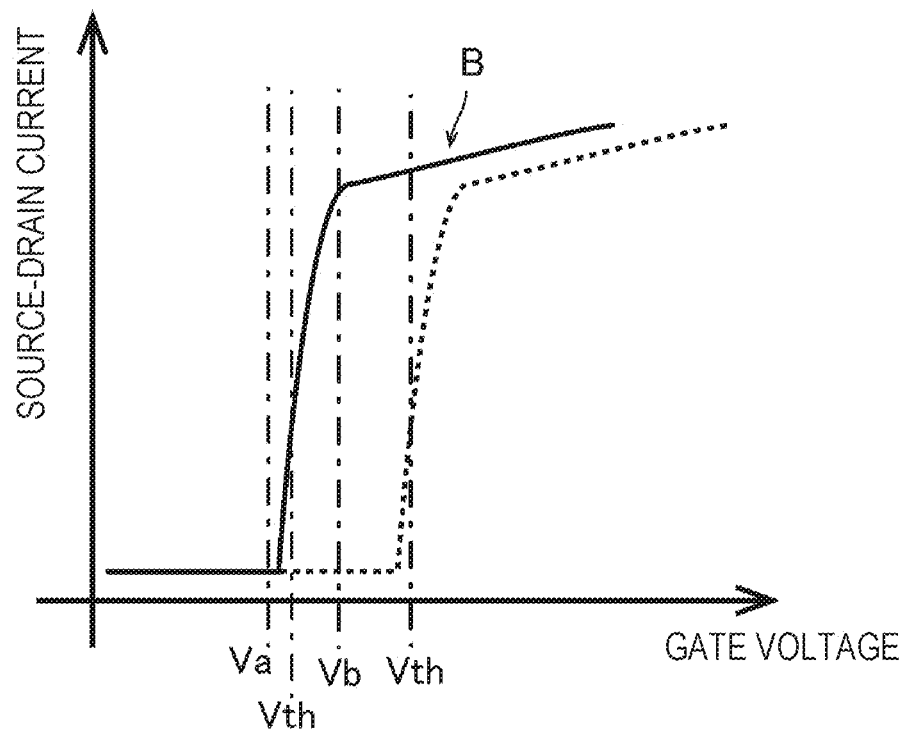
FIG. 5 illustrates a gate-off voltage in a threshold correction mode.

The X-ray imaging apparatus 100 of the first embodiment has the threshold correction mode in which a negative shift tendency of the gate-off threshold voltage Vth is detected and each TFT 14 having a negatively shifted gate-off threshold voltage Vth is corrected in terms of the gate-off threshold voltage Vth. FIG. 5 illustrates the gate-off voltage in the threshold correction mode. According to the first embodiment, a TFT 14 having a negatively shifted gate-off threshold voltage Vth is detected in the threshold correction mode. With the subject S not placed between the X-ray imaging panel 10 and the X-ray source 4, each TFT 14 is supplied with a gate signal having an inspection voltage value Vb serving as a gate-off voltage higher than the gate-off voltage Va that is supplied in the standard imaging mode. From among the TFTs 14 in the X-ray imaging panel 10, a TFT 14 having a negatively shifted gate-off threshold voltage Vth lower than the inspection voltage value Vb does not turn off but turns on. A TFT 14 having a negative shift tendency in the gate-off threshold voltage Vth is thus detected as the dark-spot pixel B. Specifically, the dark-spot pixel B that does not appear with the gate-off voltage Va in the standard imaging mode may thus be detected in the threshold correction mode.

Figure 6:
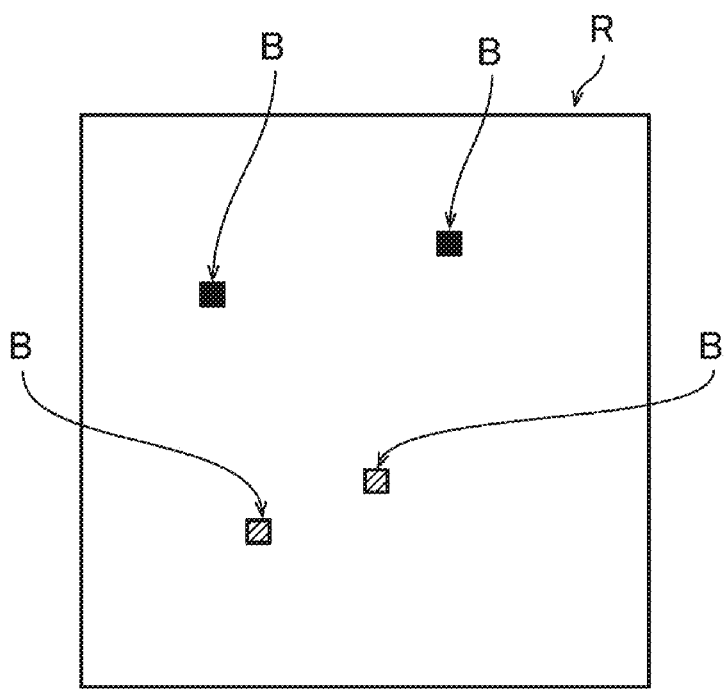
FIG. 6 illustrates an example of a captured inspection image.

FIG. 6 illustrates an example of the captured inspection image R. Referring to FIG. 6, in accordance with the data signal read from each TFT 14, the image processing unit 33b generates the inspection image R serving as a captured X-ray image used to detect the dark-spot pixel B. For example, a pixel corresponding to a TFT 14 having a negative shift tendency is included as the dark-spot pixel B in the captured inspection image R.

The detection control unit 33c detects the dark-spot pixel B from the captured inspection image R. Specifically, the detection control unit 33c calculates a mean value A of the pixel values of all pixels of the captured inspection image R and detects the dark-spot pixel B with reference to the mean value A. The dark-spot pixel B may be detected with reference to the mean value A using any detection method. For example, a pixel having a pixel value that is lower than the mean value A by a predetermined percentage or less (for example, by 10% or less) may be detected as the dark-spot pixel B. Alternatively, the detection control unit 33c may detect as the dark-spot pixel B a pixel having a pixel value that is lower than the mean value A by a predetermined deviation or less (for example, by 3σ or less). Note that σ signifies the standard deviation. In the two detection methods of the detection control unit 33c detecting the dark-spot pixel B, using the operation unit 6, a user may set to any value the magnitude of the predetermined percentage and the magnitude of the predetermined deviation. The user may set the magnitude of the predetermined percentage and the magnitude of the predetermined deviation depending on the type of the X-ray imaging apparatus 100. As described above, the dark-spot pixel B may be easily detected by comparing the mean value A with the pixel value of each pixel. The mean value A is calculated from all pixels in the captured inspection image R. Alternatively, the mean value A may be calculated from a subset of the pixels in the captured inspection image R.

Figures 7, 8:
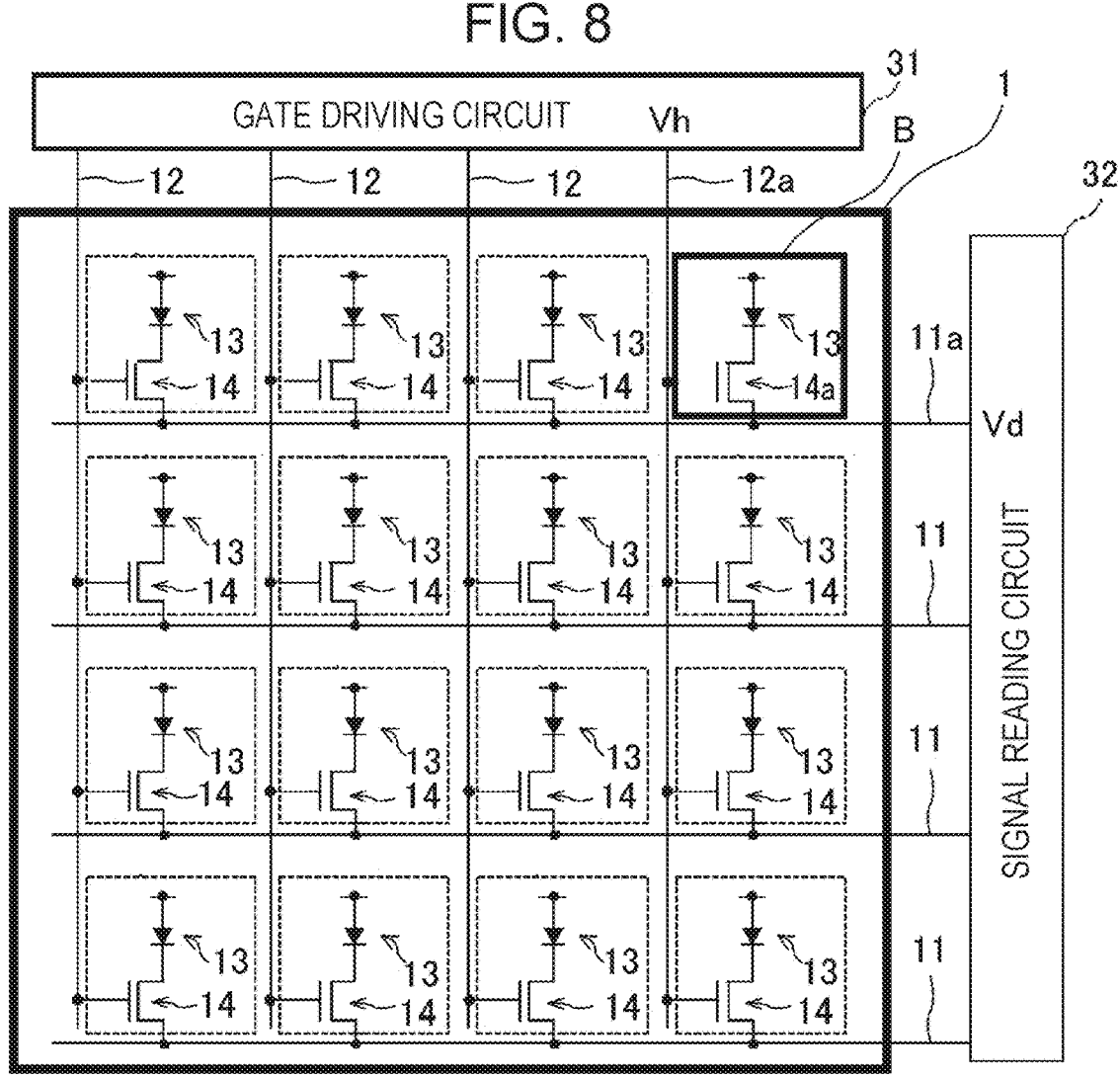
FIG. 7 illustrates an example of coordinate information on dark-spot pixels.
FIG. 8 illustrates how a positive shift voltage is applied.

FIG. 7 illustrates an example of the coordinate information 51 on the dark-spot pixels B. Referring to FIG. 7, the detection control unit 33c causes the memory 5 to store the coordinate information 51 on the detected dark-spot pixels B. For example, the coordinate information 51 includes information that identifies a pixel corresponding to a TFT 14 responsive to a gate line 12 ("542" in FIG. 7) and a data line 11 ("475" in FIG. 7). The coordinate information 51 is not limited to the example in FIG. 7 and may be any type of information that identifies coordinates on the dark-spot pixels B.

Figure 9:
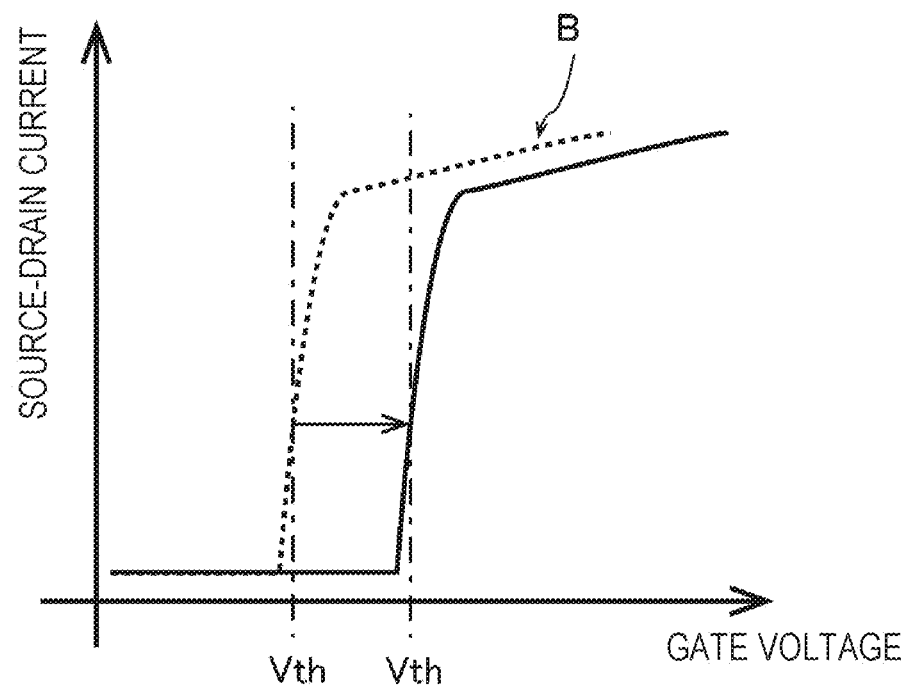
FIG. 9 illustrates positive shifting of the gate-off threshold voltage of the TFT.

FIG. 8 illustrates how the positive shift voltage Vh is applied. FIG. 9 illustrates how the gate-off threshold voltage Vth of a TFT 14a is positively shifted. Referring to FIG. 8, the TFT corresponding to the dark-spot pixel B may now be the TFT 14a. The data line connected to the TFT 14a may now be a data line 11a and the gate line connected to the TFT 14a may now be a gate line 12a. Based on the coordinate information 51 on the TFT 14a, the threshold correction unit 33d applies the positive shift voltage Vh to the gate of the TFT 14a and thus increases the gate-off threshold voltage of the TFT 14a as illustrated in FIG. 9. The gate-off threshold voltage is raised to the design value of the TFT 14. Specifically, the positive shift voltage Vh has a voltage value that enables the gate-off threshold voltage Vth to rise to the design value of the TFT 14. Referring to FIG. 9, the characteristics of the TFT 14a change from the state denoted by the broken-line curve to the state denoted by the solid-line curve. The positive shift voltage Vh has a voltage value that allows the gate-off threshold voltage Vth of the TFT 14 to rise. The voltage value is designed in advance based on the quality of the material of the TFT 14. For example, the positive shift voltage Vh has a voltage value higher than the gate-off voltage of the TFT 14a. The threshold correction unit 33d causes a voltage difference between the gate and the source of the TFT 14a by applying the positive shift voltage Vh to the gate line 12a connected to the TFT 14a and by applying a reading voltage Vd to the data line 11a connected to the TFT 14a. The threshold correction unit 33d may apply the positive shift voltage Vh to the TFT 14a only once or multiple times consecutively. The gate-off threshold voltage Vth of the TFT 14a corresponding to the dark-spot pixel B may be corrected in this way. If there are multiple dark-spot pixels B, the gate-off threshold voltages Vth of the TFTs 14a are respectively corrected in accordance with the coordinate information 51 on the TFTs 14a corresponding to the dark-spot pixels B.

In the configuration described above, not a line artifact (light spot) but a dark-spot pixel B is detected. Without employing a higher-powered X-ray source, the TFT 14a more likely to suffer from a leakage current and a negatively shifted gate-off threshold voltage Vth may be detected on a per pixel basis. The gate-off threshold voltage Vth of the TFT 14a may thus be increased by applying the positive shift voltage Vh to the TFT 14a having a negatively shifted gate-off threshold voltage Vth. Without employing a higher-powered X-ray source, image quality may be enhanced on a per pixel basis.

Control Method of First Embodiment

Figure 10:
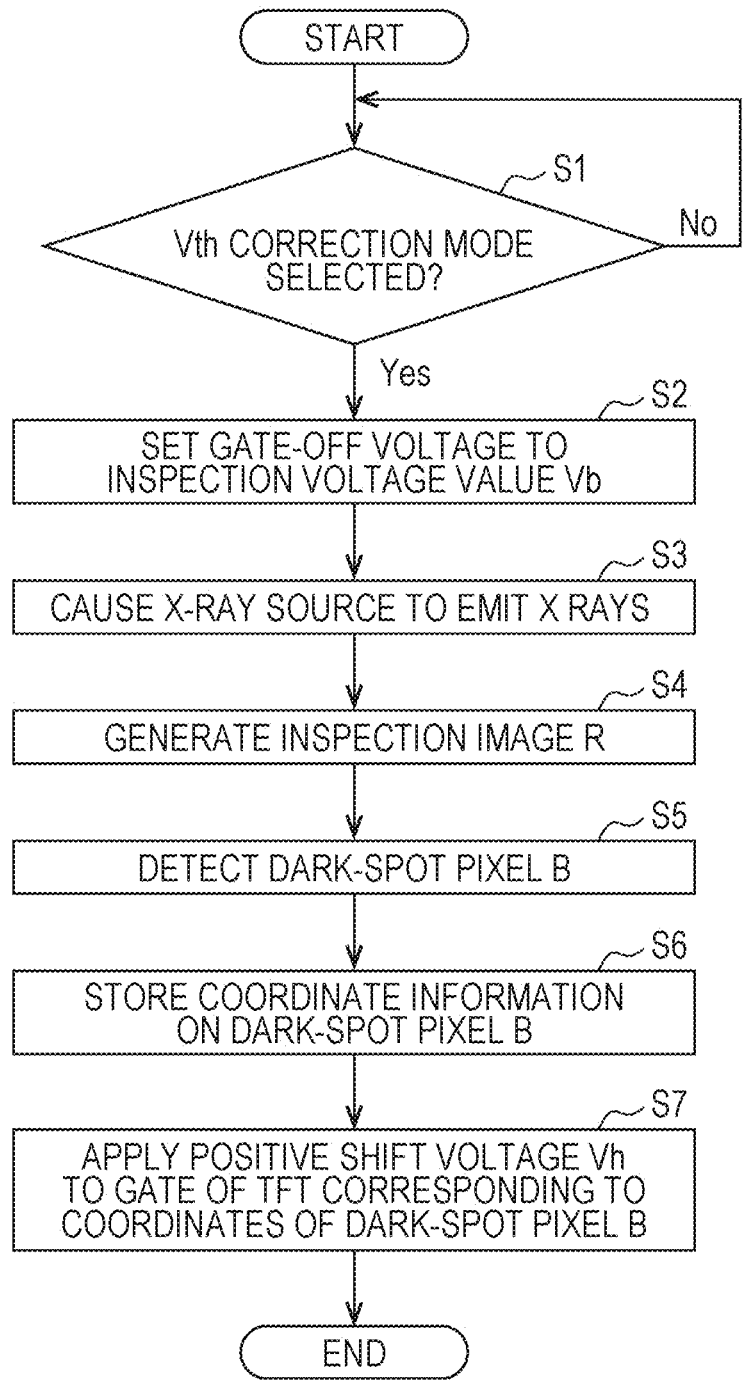
FIG. 10 is a flowchart illustrating a control process of the X-ray imaging apparatus.

A control method of the X-ray imaging apparatus 100 of the first embodiment is described below with reference to FIG. 10. FIG. 10 is a flowchart illustrating a control process of the X-ray imaging apparatus 100. The control process (in the threshold correction mode) is performed by the control circuit 33. The discussion of the control process in the standard imaging mode is omitted herein.

In step S1, the control circuit 33 determines whether the threshold correction mode has been selected. If the threshold correction mode has been selected, the process proceeds to step S2. In other words, operations in steps S2 through S7 are the control process performed in the threshold correction mode.

In step S2, the gate-off voltage is set to the inspection voltage value Vb. In step S3, the X-ray source 4 irradiates the X-ray imaging panel 10 with X rays with the subject S not placed between the X-ray source 4 and the X-ray imaging panel 10. In step S4, the gate signal including the gate-off voltage having the inspection voltage value Vb is supplied to each TFT 14. The data signal is acquired. The captured inspection image R (the captured X-ray image) is generated in accordance with the data signal.

In step S5, the dark-spot pixel B is detected from the captured inspection image R. For example, the control circuit 33 detects as the dark-spot pixel B a pixel having a pixel value that is lower than the mean value A of all pixels of the captured inspection image R by the predetermined percentage or by the predetermined deviation. In step S6, the coordinate information 51 on the detected dark-spot pixel B is stored on the memory 5.

In step S7, in accordance with the coordinate information 51, the positive shift voltage Vh is applied to the gate line 12a connected to the TFT 14a corresponding to the dark-spot pixel B and the reading voltage Vd is applied to the data line 11a connected to the TFT 14a. In this way, the gate-off threshold voltage Vth of the TFT 14a is positively shifted (rises) as illustrated in FIG. 9. The control process of the X-ray imaging apparatus 100 (the control process in the threshold correction mode) is thus complete. The image quality may be enhanced on a per pixel basis in the above described control process without employing a higher-powered X-ray source. In the threshold correction mode, a TFT 14 having a negative shift tendency may be detected and the gate-off voltage of the TFT 14 may be corrected. The control process may thus control adverse effect on the captured image caused by a negative shift in the gate-off voltage as a result of repeated use of the X-ray imaging apparatus 100.

Second Embodiment

Figure 11:
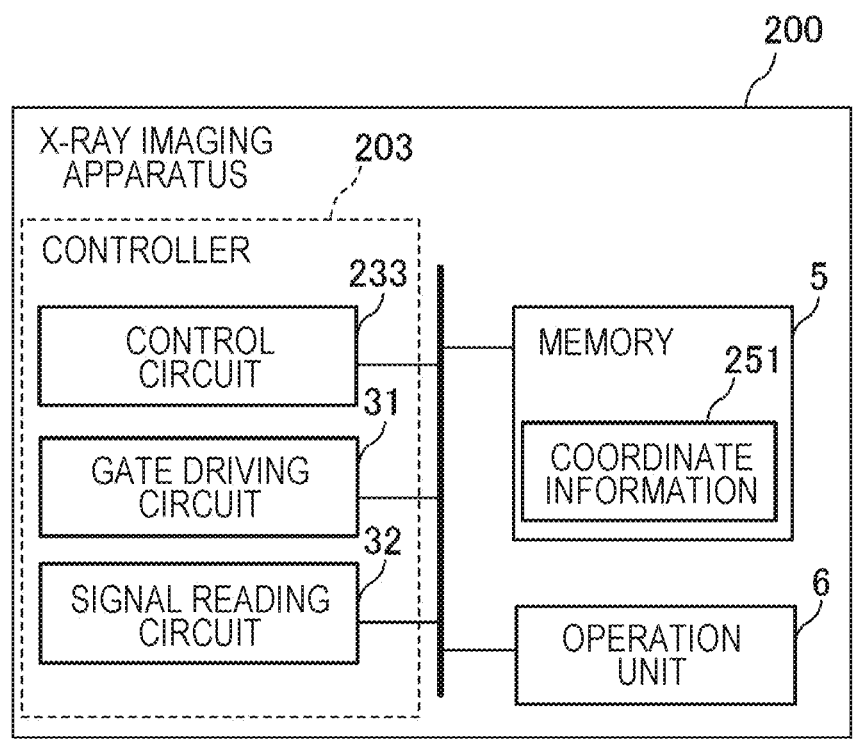
FIG. 11 is a block diagram illustrating an X-ray imaging apparatus of a second embodiment.
Figure 12:
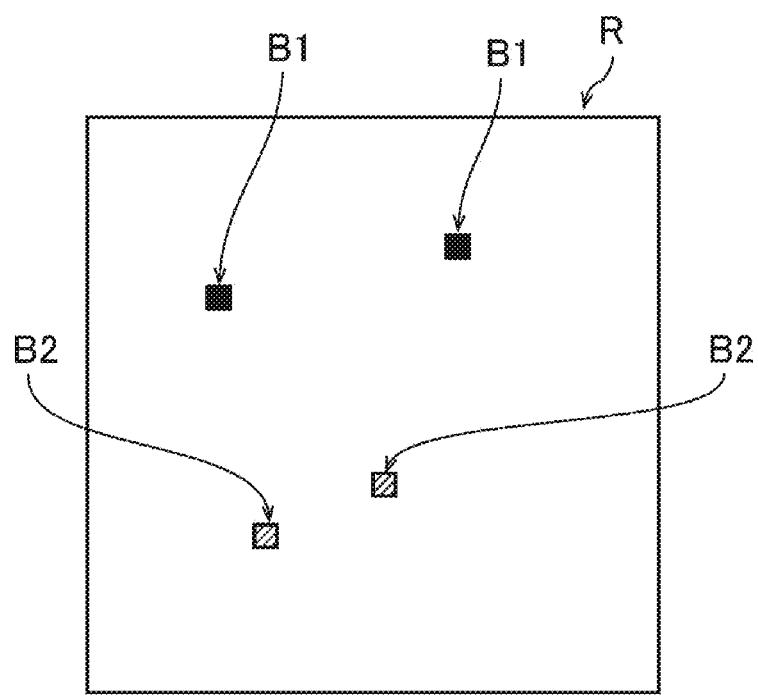
FIG. 12 illustrates how the dark-spot pixel is detected in accordance with the second embodiment.
Figures 13, 14:
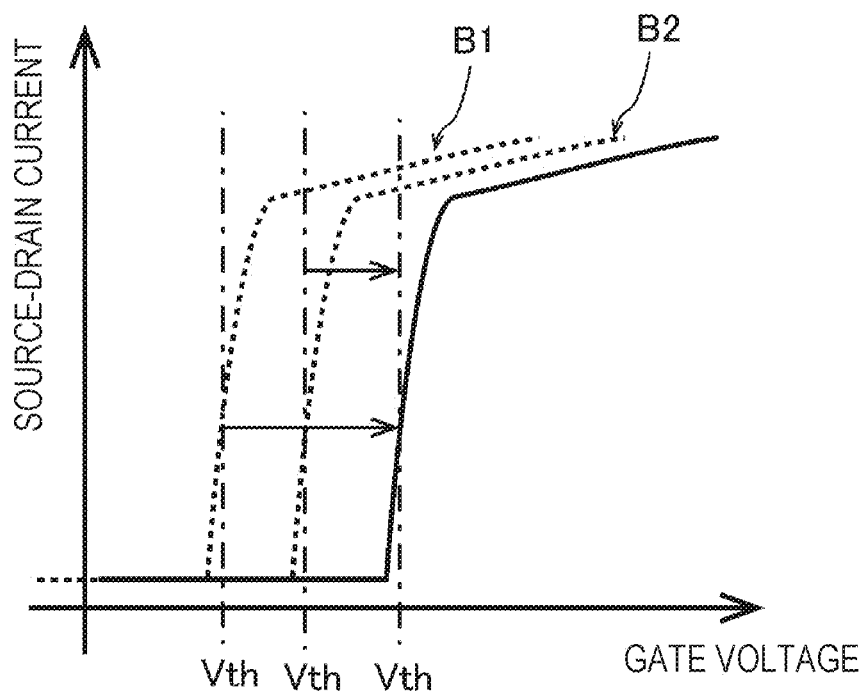
FIG. 13 illustrates coordinate information on the dark-spot pixel of the second embodiment.
FIG. 14 illustrates positive shifting of the TFT in accordance with the second embodiment.

The configuration of an X-ray imaging apparatus 200 of a second embodiment is described below with reference to FIGS. 11 through 14. FIG. 11 is a block diagram illustrating the X-ray imaging apparatus 200 of the second embodiment. FIG. 12 illustrates how the dark-spot pixels B1 and B2 are detected in accordance with the second embodiment. FIG. 13 illustrates coordinate information 251 on the dark-spot pixels B1 and B2. FIG. 14 illustrates positive shifting of the TFT 14 of the second embodiment. According to the second embodiment, the X-ray imaging apparatus 200 detects the dark-spot pixels B1 and B2 different in the degree of negative shifting and applies to the TFTs 14 positive shift voltages Vh1 and Vh2 that are responsive to the degrees of negative shifting. Elements in the second embodiment identical to elements in the first embodiment are designated with the same reference numerals and the discussion thereof is omitted herein.

Referring to FIG. 11, the X-ray imaging apparatus 200 includes a controller 203 having a control circuit 233. The memory 5 stores coordinate information 251 (see FIG. 13) on dark-spot pixels B1 and B2. The control circuit 233 (detection control unit) of the second embodiment calculates a mean value A1 of pixel values of at least two pixels (for example, all pixels) in the captured inspection image R as illustrated in FIG. 12. The control circuit 233 detects as the dark-spot pixel B2 a pixel having a pixel value that is lower than the mean value A1 by a first percentage (for example, 5%) or higher and a second percentage (for example, 10%) or lower. The control circuit 233 detects as the dark-spot pixel B1 a pixel having a pixel value that is lower than the mean value A1 by the second percentage (for example, 10%) or lower. Alternatively, the control circuit 233 detects as the dark-spot pixel B2 a pixel having a pixel value that is lower than the mean value A1 by a first deviation ($2\sigma$) or higher and a second deviation ($3\sigma$) or lower. The control circuit 233 detects as the dark-spot pixel B1 a pixel having a pixel value that is lower than the mean value A1 by the second deviation (for example, $3\sigma$) or lower. The control circuit 233 thus detects the dark-spot pixel B1 having a relatively larger degree of negative shifting and the dark-spot pixel B2 having a relatively smaller degree of negative shifting.

Referring to FIG. 13, the control circuit 233 stores the coordinate information 251 on the detected dark-spot pixels B1 and B2 onto the memory 5. Referring to FIG. 14, the control circuit 233 applies the positive shift voltage Vh1 to the gate of the TFT 14 corresponding to the dark-spot pixel B1 and the positive shift voltage Vh2 lower than the positive shift voltage Vh1 to the gate of the TFT 14 corresponding to the dark-spot pixel B2. The gate-off threshold voltage Vth of the TFT 14 corresponding to the dark-spot pixel B1 thus positively shifts and the gate-off threshold voltage Vth of the TFT 14 corresponding to the dark-spot pixel B2 positively shifts. The rest of the configuration and effect of the second embodiment is identical to the configuration and effect of the first embodiment.

Third Embodiment

Figure 15:
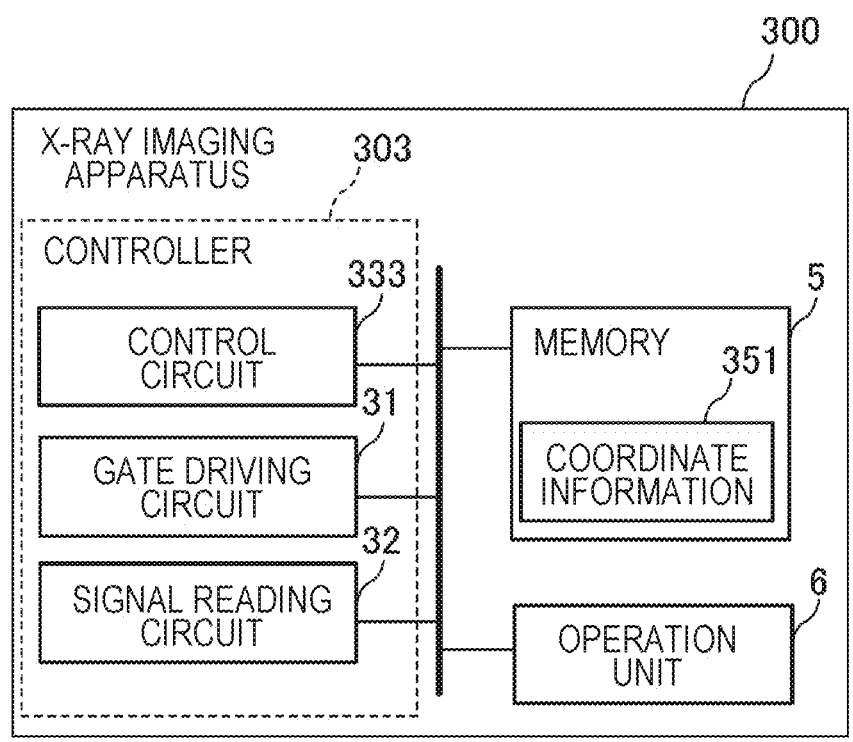
FIG. 15 is a block diagram illustrating an X-ray imaging apparatus of a third embodiment.
Figure 16A:
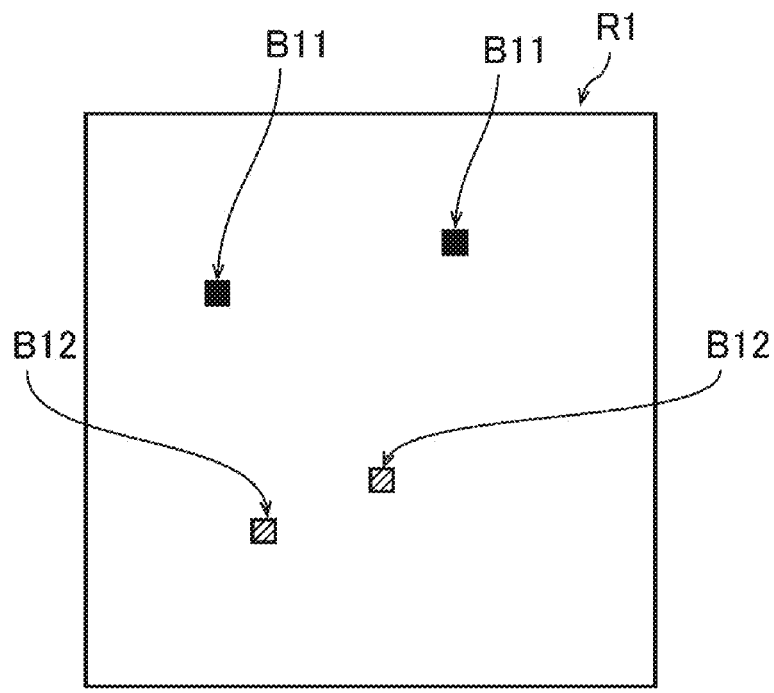
FIG. 16A illustrates an example of a captured inspection image generated in accordance with an inspection voltage value.
Figure 16B:
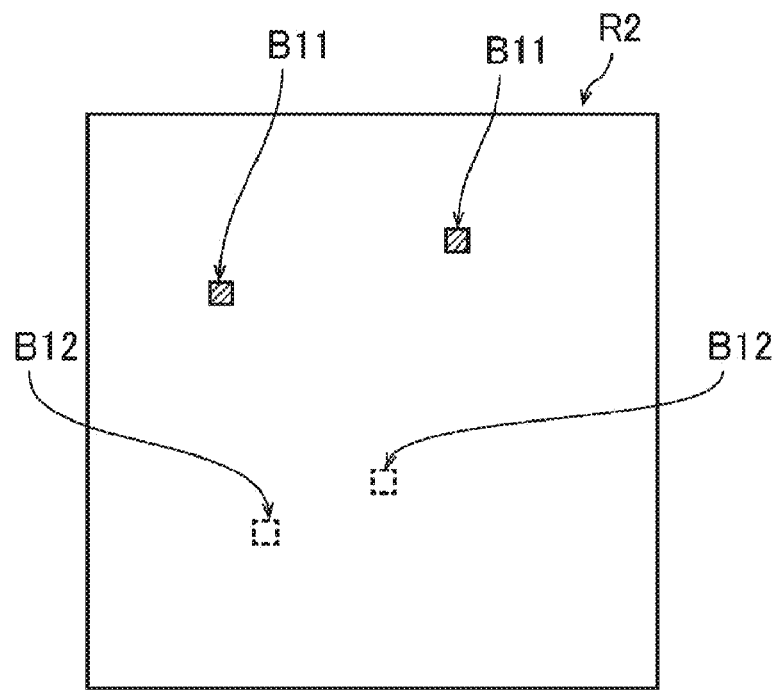
FIG. 16B illustrates an example of another inspection image generated in accordance with another inspection voltage value.
Figures 17, 18:
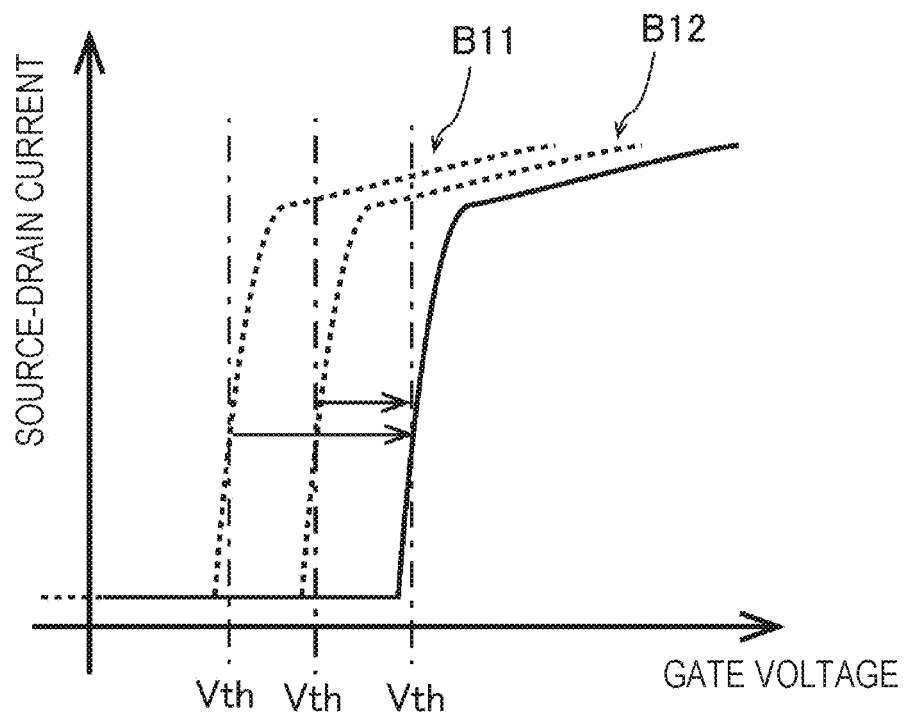
FIG. 17 illustrates coordinate information on dark-spot pixels of the third embodiment.
FIG. 18 illustrates positive shifting of the TFT in accordance with the third embodiment.

An X-ray imaging apparatus 300 of a third embodiment is described with reference to FIGS. 15 through 17. FIG. 15 is a block diagram illustrating the X-ray imaging apparatus 300 of the third embodiment. FIG. 16A illustrates an example of a captured inspection image R1 generated in accordance with an inspection voltage value Vb1. FIG. 16B illustrates an example of a captured inspection image R2 generated in accordance with an inspection voltage value Vb2. FIG. 17 illustrates coordinate information 351 on dark-spot pixels B11 and B12. FIG. 18 illustrates positive shifting of the TFT 14 of the third embodiment. In accordance with the third embodiment, the X-ray imaging apparatus 300 generates captured inspection images R1 and R2 using the inspection voltage values Vb1 and Vb2 at two separate voltage levels and detects dark-spot pixels B11 and B12 different in the degree of negative shifting. Elements of the third embodiment identical to the elements of the first and second embodiments are designated with the same reference numerals and the discussion thereof is omitted herein.

Referring to FIG. 15, the X-ray imaging apparatus 300 includes a controller 303 having a control circuit 333. The memory 5 stores the coordinate information 351 (see FIG. 17) on the dark-spot pixels B11 and B12. The control circuit 333 (image processing unit) of the third embodiment generates the captured inspection image R1, as illustrated in FIG. 16A, in accordance with the data signal that is acquired using the gate-off voltage having the inspection voltage value Vb1 higher than the voltage value Va used when the subject S is imaged. The control circuit 333 (image processing unit) generates the captured inspection image R2, as illustrated in FIG. 16B, in accordance with the data signal that is acquired using the gate-off voltage having the inspection voltage value Vb2 that is equal to or higher than the voltage value Va and lower than the inspection voltage value Vb1.

The control circuit 333 (detection control unit) of the third embodiment detects, as the dark-spot pixel B11 having a larger degree of negative shifting, a pixel detected as the dark-spot pixel B, in both the captured inspection image R1 and the captured inspection image R2. The control circuit 333 (detection control unit) of the third embodiment detects, as the dark-spot pixel B12 having a relatively smaller degree of negative shifting, a pixel detected as the dark-spot pixel B, in only the captured inspection image R1. Referring to FIG. 17, the control circuit 333 causes the memory 5 to store the coordinate information 351 on the detected dark-spot pixels B11 and B12. Referring to FIG. 18, the control circuit 333 applies a positive shift voltage Vh11 to the gate of the TFT 14 corresponding to the dark-spot pixel B11 and applies a positive shift voltage Vh12, lower than the positive shift voltage Vh11, to the gate of the TFT 14 corresponding to the dark-spot pixel B12. The gate-off threshold voltage Vth of the TFT 14 corresponding to the dark-spot pixel B11 is positively shifted and the gate-off threshold voltage Vth of the TFT 14 corresponding to the dark-spot pixel B12 is positively shifted. The rest of the configuration and effect of the third embodiment is identical to the configuration and effect of the first embodiment.

Control Method of Third Embodiment

Figure 19:
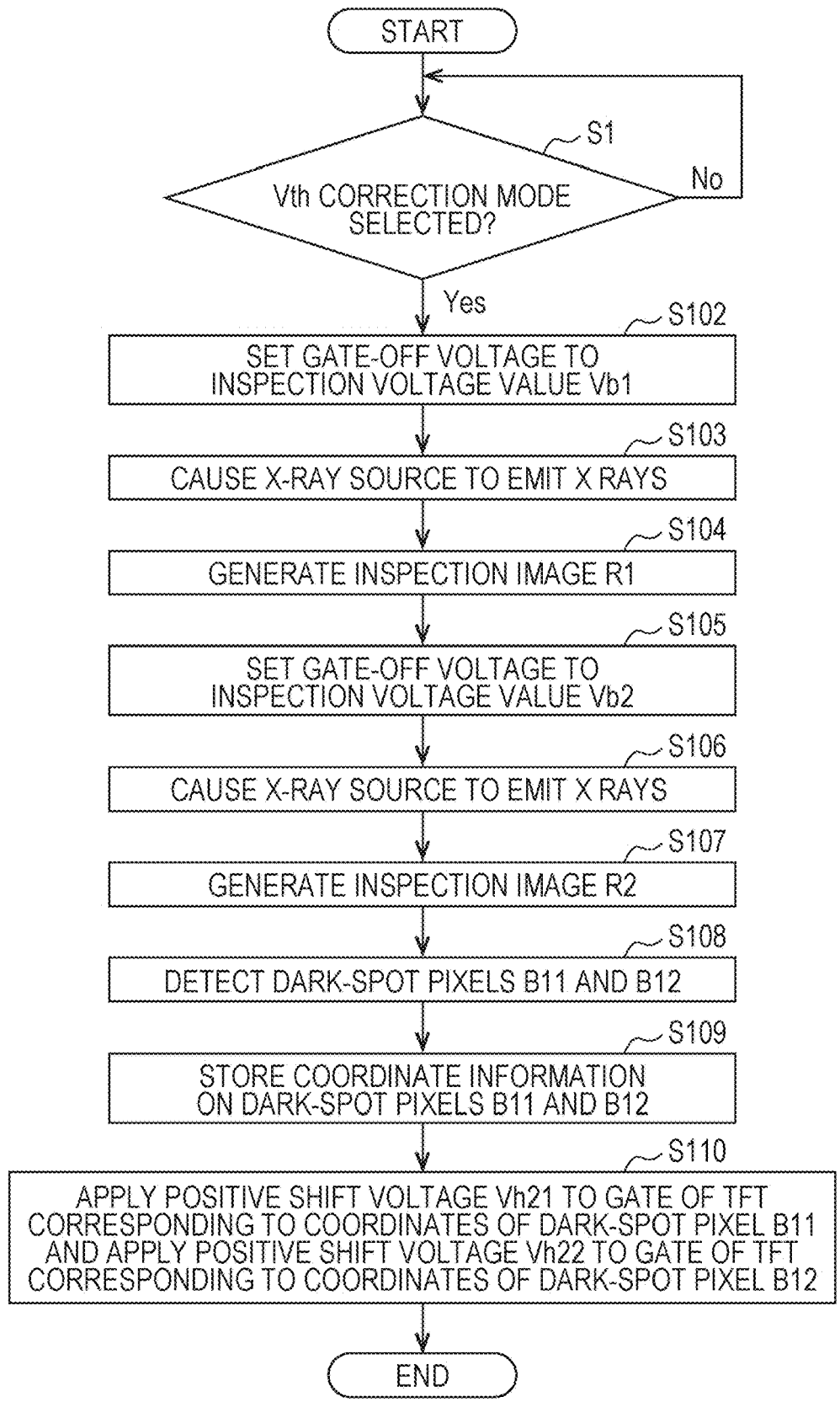
FIG. 19 is a flowchart illustrating a control process of the X-ray imaging apparatus of the third embodiment.

A control method of the X-ray imaging apparatus 300 of the third embodiment is described with reference to FIG. 19. FIG. 19 is a flowchart illustrating a control process of the X-ray imaging apparatus 300. The control process is performed by the control circuit 333.

In step S1, the control circuit 333 determines whether the threshold correction mode has been selected. If the threshold correction mode has been selected, the process proceeds to step S102. In step S102, the gate-off voltage is set to the inspection voltage value Vb1. In step S103, the X-ray source 4 irradiates the X-ray imaging panel 10 with X rays with the subject S not placed between the X-ray source 4 and the X-ray imaging panel 10. In step S104, the gate signal including the gate-off voltage having the inspection voltage value Vb1 is supplied to each TFT 14. The data signal is acquired and the captured inspection image R1 is generated in accordance with the data signal.

In step S105, the gate-off voltage is set to the inspection voltage value Vb2. In step S106, the X-ray source 4 irradiates the X-ray imaging panel 10 with X rays with the subject S not placed between the X-ray source 4 and the X-ray imaging panel 10. In step S107, the gate signal including the gate-off voltage having the inspection voltage value Vb2 is supplied to each TFT 14. The data signal is acquired and the inspection image R2 is generated in accordance with the data signal.

In step S108, the dark-spot pixels B11 and B12 are detected from the captured inspection images R1 and R2. For example, a pixel detected as a dark-spot pixel is detected as the dark-spot pixel B11 from both of the captured inspection images R1 and R2 and a pixel detected as a dark-spot pixel is detected as the dark-spot pixel B12 from only the captured inspection image R1. In step S109, the memory 5 stores the coordinate information 351 on the detected dark-spot pixels B11 and B12.

In step S110, based on the coordinate information 351, a positive shift voltage Vh21 is applied to the gate line 12 connected to the TFT 14 corresponding to the coordinates of the dark-spot pixel B11 and the reading voltage Vd is applied to the data line 11 connected to the TFT 14. Based on the coordinate information 351, a positive shift voltage Vh22 is applied to the gate line 12 connected to the TFT 14 corresponding to the coordinates of the dark-spot pixel B12 and the reading voltage Vd is applied to the data line 11 connected to the TFT 14. Referring to FIG. 18, the gate-off threshold voltage Vth of the TFT 14 shifts positively (rises).

The control process of the X-ray imaging apparatus 300 (the control process in the threshold correction mode) thus ends.

The embodiments have been described for exemplary purposes only. The disclosure is not limited to the embodiments. The embodiments may be changed or modified without departing from the scope of the disclosure.

(1) According to the first through third embodiments, the threshold correction mode may be performed in response to an operation of a user on the operation unit. The disclosure is not limited to this manner. Alternatively, the threshold correction mode may be performed in a manner free from the operation of the user.

(2) According to the first through third embodiments, the detection of the dark-spot pixel and the application of the positive shift voltage to the gate of the TFT are performed consecutively in the control process as illustrated in FIG. 10. The disclosure is not limited to this manner. The detection of the dark-spot pixel and the application of the positive shift voltage to the gate of the TFT may be performed at different timings. For example, after the detection of the dark-spot pixel B are repeated several times, the application of the positive shift voltage to the gate of the TFT may be performed once.

(3) According to the first through third embodiments, in order to generate the captured inspection image, an inspection voltage value is set to a voltage different from the gate-off voltage used to image the subject (standard gate-off voltage). The disclosure is not limited to this manner. For example, in order to generate the captured inspection image, the inspection voltage value may be set to a voltage identical to the gate-off voltage used to image the subject (standard gate-off voltage).

(4) According to the first through third embodiments, in order to detect the dark-spot pixel, the mean value of all pixels in the captured inspection image is calculated. The disclosure is not limited to this manner. For example, the mean value of a subset of the pixels in the captured inspection image may be calculated.

(5) According to the first through third embodiments, the mean value of the pixels in the captured inspection image is calculated to detect the dark-spot pixel. The disclosure is not limited to this manner. For example, the median value or the mode value of the pixel values of the pixels in the captured inspection image may be calculated. Any method of detecting the dark-spot pixel in accordance with the median value or the mode value may be utilized. For example, if the median value is calculated, a pixel having a pixel value smaller than the median value by a predetermined percentage may be detected as the dark-spot pixel or a pixel having a pixel value smaller than the median value by a predetermined deviation may be detected as the dark-spot pixel B. If the mode value is calculated, a pixel having a pixel value smaller than the mode value by a predetermined percentage may be detected as the dark-spot pixel or a pixel having a pixel value smaller than the mode value by a predetermined deviation may be detected as the dark-spot pixel.

The X-ray imaging apparatus and the control method thereof may be described as below.

According to a first configuration, there is provided an X-ray imaging apparatus including an X-ray source; an X-ray imaging panel including a scintillator that converts X rays emitted from the X-ray source into light, a photoelectric conversion element that converts the light from the scintillator into an electrical signal, and a thin-film transistor connected to the photoelectric conversion element; and a controller that controls emission of the X rays from the X-ray source and imaging performed by the X-ray imaging panel. The controller includes: an image processing unit that generates an inspection image that is captured with a subject not placed between the X-ray source and the X-ray imaging panel in accordance with a data signal that is read from the thin-film transistor supplied with a gate signal; a detection control unit that detects a dark-spot pixel from the inspection image; and a threshold correction unit that applies, to a gate of a thin-film transistor corresponding to the dark-spot pixel, a positive shift voltage that raises a gate-off threshold voltage of the thin-film transistor (first configuration).

In the first configuration, not a line artifact (light spot) but a dark-spot pixel B is detected. Without employing a higher-powered X-ray source, a thin-film transistor (TFT) likely to suffer from a leakage current may be detected. By detecting the dark-spot pixel, the TFT having a negatively shifted gate-off voltage may be detected on a per pixel basis. Since the gate-off voltage of the TFT is increased by applying a positive shift voltage to the negatively shifted TFT, image quality may be enhanced on a per pixel basis.

In the first configuration, the image processing unit may supply the thin-film transistor with a gate signal having an inspection voltage value serving as a gate-off voltage higher than a gate-off voltage that is supplied to the thin-film transistor when the subject is imaged, and the image processing unit may generate the inspection image in accordance with the data signal read from the thin-film transistor (second configuration).

In the second configuration, since a dark-spot pixel that does not appear with the gate-off voltage used to image the subject (in the standard imaging mode) is detected, the gate-off voltage of the TFT may be positively shifted before the subject is imaged. As a result, no dark-spot pixel appears when the subject is imaged. Image quality may thus be enhanced.

In the first or second configuration, the X-ray imaging apparatus may further include a memory, the detection control unit may cause the memory to store information on coordinates of the dark-spot pixel, and the threshold correction unit may apply the positive shift voltage to the gate of the thin-film transistor specified by the information on the coordinates (third configuration).

In the third configuration, the TFT serving as a target that is supplied with a positive shift voltage may be easily identified in accordance with the information on the coordinates stored on the memory.

In one of the first through third configurations, the detection control unit may detect as the dark-spot pixel a pixel having a pixel value that is lower by a predetermined value than one of a mean value, a median value, and a mode value of two or more pixels of the inspection image (fourth configuration).

In the fourth configuration, the dark-spot pixel may be easily detected by comparing the pixel value of each pixel with one of the mean value, the median value, and the mode value.

According to a fifth configuration, there is provided a control method of an X-ray imaging apparatus including an X-ray source, and an X-ray imaging panel that includes a scintillator that converts X rays emitted from the X-ray source into light, a photoelectric conversion element that converts the light from the scintillator into an electrical signal, and a thin-film transistor connected to the photoelectric conversion element. The control method include: irradiating the X-ray imaging panel with the X rays from the X-ray source; acquiring an inspection image that is captured with a subject not placed between the X-ray source and the X-ray imaging panel in accordance with a data signal that is read from the thin-film transistor supplied with a gate signal; detecting a dark-spot pixel from the inspection image; and applying, to a gate of a thin-film transistor corresponding to the dark-spot pixel, a positive shift voltage that raises a gate-off threshold voltage of the thin-film transistor (fifth configuration).

In the fifth configuration as in the same way in the first configuration, image quality may be enhanced on a per pixel basis without employing a higher-powered X-ray source.

The present disclosure contains subject matter related to that disclosed in Japanese Priority Patent Application JP 2021-095281 filed in the Japan Patent Office on Jun. 7, 2021, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. An X-ray imaging apparatus comprising:
an X-ray source;
an X-ray imaging panel including a scintillator that converts X rays emitted from the X-ray source into light, a photoelectric conversion element that converts the light from the scintillator into an electrical signal, and a thin-film transistor connected to the photoelectric conversion element; and
a controller that controls emission of the X rays from the X-ray source and imaging performed by the X-ray imaging panel,
wherein the controller includes:
an image processing unit that generates an inspection image that is captured with a subject not placed between the X-ray source and the X-ray imaging panel in accordance with a data signal that is read from the thin-film transistor supplied with a gate signal;
a detection control unit that detects a dark-spot pixel from the inspection image; and
a threshold correction unit that applies, to a gate of a thin-film transistor corresponding to the dark-spot pixel, a positive shift voltage that raises a gate-off threshold voltage of the thin-film transistor.

2. The X-ray imaging apparatus according to claim 1, wherein the image processing unit supplies the thin-film transistor with a gate signal having an inspection voltage value serving as a gate-off voltage higher than a gate-off voltage that is supplied to the thin-film transistor when the subject is imaged, and the image processing unit generates the inspection image in accordance with the data signal read from the thin-film transistor.

3. The X-ray imaging apparatus according to claim 1, further comprising a memory,
wherein the detection control unit causes the memory to store information on coordinates of the dark-spot pixel, and
wherein the threshold correction unit applies the positive shift voltage to the gate of the thin-film transistor specified by the information on the coordinates.

4. The X-ray imaging apparatus according to claim 1, wherein the detection control unit detects as the dark-spot pixel a pixel having a pixel value that is lower by a predetermined value than one of a mean value, a median value, and a mode value of two or more pixels of the inspection image.

5. A control method of an X-ray imaging apparatus including an X-ray source, and an X-ray imaging panel that includes a scintillator that converts X rays emitted from the X-ray source into light, a photoelectric conversion element that converts the light from the scintillator into an electrical signal, and a thin-film transistor connected to the photoelectric conversion element, the control method comprising:
- irradiating the X-ray imaging panel with the X rays from the X-ray source;
- acquiring an inspection image that is captured with a subject not placed between the X-ray source and the X-ray imaging panel in accordance with a data signal that is read from the thin-film transistor supplied with a gate signal;
- detecting a dark-spot pixel from the inspection image; and
- applying, to a gate of a thin-film transistor corresponding to the dark-spot pixel, a positive shift voltage that raises a gate-off threshold voltage of the thin-film transistor.

* * * * *